(12) United States Patent
Palepu

(10) Patent No.: US 9,801,892 B2
(45) Date of Patent: *Oct. 31, 2017

(54) FULVESTRANT FORMULATIONS

(71) Applicant: HAZ TWO, LLC, Amherst, MA (US)

(72) Inventor: Nageswara R. Palepu, Southampton, PA (US)

(73) Assignee: HAZ TWO, LLC, Amherst, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/934,428

(22) Filed: Nov. 6, 2015

(65) Prior Publication Data

US 2016/0058773 A1    Mar. 3, 2016

Related U.S. Application Data

(62) Division of application No. 12/380,968, filed on Mar. 5, 2009, now Pat. No. 9,180,088.

(60) Provisional application No. 61/068,560, filed on Mar. 7, 2008.

(51) Int. Cl.
| | |
|---|---|
| *A61K 31/565* | (2006.01) |
| *A61K 47/10* | (2017.01) |
| *A61K 47/20* | (2006.01) |
| *A61K 47/22* | (2006.01) |
| *A61K 9/00* | (2006.01) |
| *A61K 9/08* | (2006.01) |

(52) U.S. Cl.
CPC .......... *A61K 31/565* (2013.01); *A61K 9/0019* (2013.01); *A61K 9/08* (2013.01); *A61K 47/10* (2013.01); *A61K 47/20* (2013.01); *A61K 47/22* (2013.01); *A61K 9/0014* (2013.01)

(58) Field of Classification Search
CPC ...... A61K 31/565; A61K 47/10; A61K 47/20; A61K 47/22; A61K 9/0014; A61K 9/0019; A61K 9/08

See application file for complete search history.

(56) References Cited

U.S. PATENT DOCUMENTS

| | | | |
|---|---|---|---|
| 4,659,516 A | 4/1987 | Bowler et al. | |
| 5,462,726 A | 10/1995 | Lodge | |
| 6,531,139 B1 | 3/2003 | Gao et al. | |
| 6,774,122 B2 | 8/2004 | Evans et al. | |
| 7,115,565 B2 | 10/2006 | Gao et al. | |
| 2002/0049158 A1 | 4/2002 | Woo et al. | |
| 2002/0102280 A1 | 8/2002 | Anderson | |
| 2004/0047835 A1* | 3/2004 | Bianco | A61K 31/00 424/78.17 |
| 2004/0175402 A1 | 9/2004 | Gellert et al. | |
| 2005/0043285 A1* | 2/2005 | Evans | A61K 9/0019 514/182 |
| 2006/0003002 A1 | 1/2006 | Fikstad et al. | |
| 2006/0172014 A1 | 8/2006 | Curd et al. | |
| 2006/0189679 A1 | 8/2006 | Holton et al. | |
| 2006/0264357 A1 | 11/2006 | Zikria et al. | |
| 2007/0116729 A1 | 5/2007 | Palepu | |
| 2007/0237740 A1* | 10/2007 | Reddington | A61K 9/0024 424/78.08 |
| 2007/0269379 A1 | 11/2007 | Mittagotri et al. | |
| 2007/0281934 A1 | 12/2007 | Buggy et al. | |
| 2008/0146651 A1 | 6/2008 | Jee et al. | |
| 2008/0319048 A1 | 12/2008 | Palepu et al. | |
| 2009/0181068 A1 | 7/2009 | Dunn | |
| 2009/0227549 A1 | 9/2009 | Palepu | |
| 2009/0318543 A1 | 12/2009 | Vu et al. | |
| 2010/0015195 A1 | 1/2010 | Jain et al. | |

FOREIGN PATENT DOCUMENTS

| | | |
|---|---|---|
| GB | 2087721 A | 6/1982 |
| KR | 1020100018741 | 2/2010 |
| WO | 97/21440 A1 | 6/1997 |
| WO | 01/51056 A1 | 7/2001 |
| WO | 02092077 A2 | 11/2002 |
| WO | 2005039554 A2 | 5/2005 |
| WO | 2005097105 A1 | 10/2005 |
| WO | 2007020085 | 2/2007 |
| WO | 2007033434 A1 | 3/2007 |
| WO | 2009090614 A2 | 7/2009 |
| WO | 2009111057 A2 | 9/2009 |

OTHER PUBLICATIONS

Weller, "Glycofurol", Handbook of Pharmaceutical Excipients, 5th ed., 2006, pp. 313-314.
Supplementary European Search Report based on Application No. EP 09716692, dated Sep. 18, 2013. (2 pages).
Chinese Office action based on Chinese Application No. 200980108157.3 dated Nov. 7, 2011 ( 9 pages).
Du Wenting, et al. "Research progression of water-soluble derivatives of paclitaxe", The Chinese Journal of Modern Applied Pharmacy, vol. 22, No. 1, pp. 29-31.
Japanese Office action based on Japanese Application No. 2010-549670 dated Aug. 6, 2013 (5 pages). (English Translation).
Written Opinion of the International Searching Authority based on International Application No. PCT/IN2013/000235, dated Oct. 14, 2014 (7 pages).
International Search Report based on International Application No. PCT/IN2013/000235 dated Aug. 12, 2013 (4 pages).
Scientific Discussion, EMEA. Nov. 21, 2006, pp. 1-33 (Retrieved from Internet: URL: http://web.archive.org/web/20061121015215// http://www.emea.europa.eu/humandocs/PDFs/EPAR/faslodex/ 610303en6.pdf).
Bross et al., Fulvestrant in Postmenopausal Women with Advanced Breast Cancer, Clinical Cancer Research. Oct. 1, 2003, vol. 9 pp. 4309-4317.
Castor Oil MSDS Material Safety Data Sheet, Science Lab.com Chemiicals & Laboratory Equipment. Mar. 23, 2006, pp. 1 (Retrieved from Internet: URL: http://web.archive.org/web/ 20060323231047/http:/www.sciencelab.com/xMSDS-Castor_oil-9927126.

(Continued)

*Primary Examiner* — Snigdha Maewall
(74) *Attorney, Agent, or Firm* — Lucas & Mercanti, LLP

(57) ABSTRACT

Fulvestrant formulations suitable for intramuscular injection at concentration in excess of 40 mg/ml in the absence of castor oil and castor oil derivatives are disclosed.

22 Claims, No Drawings

(56) References Cited

OTHER PUBLICATIONS

PCT Search Report and Written Opinion of the International Search Authority in PCT/US09/01437.

* cited by examiner

FULVESTRANT FORMULATIONS

CROSS-REFERENCE TO RELATED APPLICATIONS

This application is a divisional application of U.S. patent application Ser. No. 12/380,968 filed on Mar. 5, 2009, which, in turn claims the benefit of priority from of U.S. provisional Application Ser. No. 61/068,560, filed Mar. 7, 2008, the contents of each of which are incorporated herein by reference in their entirety.

STATEMENT REGARDING FEDERALLY SPONSORED RESEARCH OR DEVELOPMENT

Not Applicable

FIELD OF THE INVENTION

The present invention relates to fulvestrant formulations, especially to injectable formulations of fulvestrant, and particularly to intramuscular injectable formulations. The invention also related to the solvents glycofurol, poloxamer, reverse poloxamer, polyethylene glycol, propylene glycol, and dihydrolipoic acid.

BACKGROUND OF THE INVENTION

Fulvestrant Injection for intramuscular administration is an estrogen receptor antagonist without known agonist effects and is marketed by Astra-Zeneca under trade name Faslodex®. The chemical name is 7-alpha-[9-(4,4,5,5,5-penta fluoropentylsulphinyl) nonyl]estra-1,3,5-(10)-triene-3,17-beta-diol. The molecular formula is $C_{32}H_{47}F_5O_3S$ and its structural formula is:

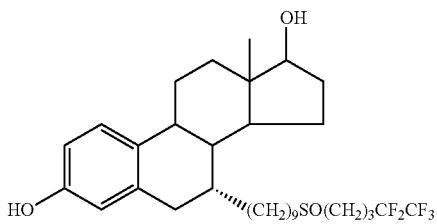

Fulvestrant is a white powder with a molecular weight of 606.77. The solution for injection (as currently marketed) is a clear, colorless to yellow, viscous liquid. Each injection of the currently marketed FASLODEX contains as inactive ingredients: Alcohol, USP; Benzyl Alcohol, NF; and Benzyl Benzoate, USP, as co-solvents; and Castor Oil, USP as a co-solvent and release rate modifier. Its manufacture and general use are disclosed in U.S. Pat. No. 4,659,516, which is incorporated herein by reference in its entirety.

FASLODEX is supplied in sterile single patient pre-filled syringes containing 50 mg/ml fulvestrant either as a single 5 ml or two concurrent 2.5 ml injections to deliver the required monthly dose. Fulvestrant is currently labeled in the currently marketed FASLODEX product to be administered as an intramuscular injection of 250 mg once monthly.

A formulation of fulvestrant for intramuscular injection is disclosed in U.S. Pat. No. 6,774,122, which is incorporated herein by reference in its entirety. The formulation claimed in that patent is a fulvestrant solution in a ricinoleate vehicle that additionally has at least one alcohol and a non-aqueous solvent which is miscible with the ricinoleate vehicle. The currently marketed FASLODEX injection product contains, in addition to the fulvestrant; alcohol USP; benzyl alcohol; benzyl benzoate; and castor oil. Castor oil administration by injection has been associated with potential side effects. In fulvestrant formulations having castor oil, injection site irritation is one of the most common side effects. Ricinoleate (the major component of castor oil) is an intestinal secretogogue. Zinc ricinoleate has been found to be a sensitizer in deodorants in which it has been incorporated. Sodium ricinoleate has been found to have membrane disruptive effects. Type IV dermal sensitization response in those previously sensitized to ricinoleate have been attributed to ricinoleate administration. U.S. Pat. No. 5,462,726 is directed to a method of reducing, inhibiting, or treating the unwanted side effects of castor oil in a solvent in a drug formulation by administering a thromboxane $A_2$ receptor antagonist. Thus, it is clear that the art recognizes there are concerns about administering castor oil and castor oil derivatives as pharmaceutical excipients, especially by injection or transdermal routes. And, while these side effects may have to be accepted when there is no other material which is suitable for administering a drug in an appropriate manner, the search for a suitable alternative without these side effects, or lesser degree of these side effects, continues, and the discovery of such an appropriate alternative would meet a long felt unmet need in the art.

In addition, there has been increasing interest in administration of fulvestrant at doses in excess of the currently labeled amounts, up to and including as much as 1 gram per month. To do so with current formulations, would currently require considerably larger volumes than could be injected intramuscularly at any one time (5 ml being about the most possible), use of multiple injection sites, or administration at multiple times throughout the month. Ideally, one would like to administer the full desired dose at one time and at one injection site. With the currently marketed fulvestrant products, this is currently impossible. Thus the search for injectable formulations of fulvestrant that can deliver more than 250 mg in less than 5 ml of formulation is a sought after end in the art.

OBJECTS OF THE INVENTION

It is therefore an object of the invention to provide a formulation of fulvestrant that is suitable for injection purposes that is substantially free of, if not totally free of, castor oil and castor oil derivatives.

It is a further object of the invention is to provide a method of administering fulvestrant by injection that is substantially free of, if not totally free of, injection site irritation.

It is yet another object of the invention is to provide an intramuscular injection formulation of fulvestrant being substantially free, if not totally free of, castor oil and castor oil derivatives.

Still another object of the invention is to provide a method of administering fulvestrant by intramuscular injection that is substantially free of, if not totally free of, injection site irritation.

Still an additional object of the invention is to provide a method of administering the recommended dose of fulvestrant with reduced volume (i.e., 1-4 ml relative to currently marketed Faslodex of 5 ml) at the injection site.

Yet another object of the invention is to provide an injectable formulation of fulvestrant that can deliver dosages of up to 1 gram of fulvestrant in volumes of less than 5 ml of formulation.

A further object of the invention is to provide a transdermal administrable formulation of fulvestrant that is substantially free, if not totally free of, castor oil and castor oil derivatives.

An even further object of the invention is to provide a method of administering a fulvestrant formulation transdermally that is substantially free of side effects associated with castor oil and castor oil derivatives.

A still further object of the invention is the provision of a fulvestrant formulation for injection or transdermal administration in which the fulvestrant is present in a vehicle containing at least one solvent selected from polyethylene glycol, propylene glycol, glycofurol, poloxamer, reverse poloxamer, dihydrolipoic acid, mixtures thereof, and nonaqueous solutions of the foregoing.

An even further object of the invention is to provide an intramuscular injection dosage form of fulvestrant that is capable of delivering a therapeutically effective amount of fulvestrant in less than 5 ml of formulation.

Still another object of the invention is to provide a fulvestrant intramuscular injection dosage form that can deliver a therapeutically effective amount of fulvestrant in a single injection of about or less than 2.5 ml of formulation.

Still another object of the invention is to provide a fulvestrant intramuscular injection dosage form that can deliver a therapeutically effective amount of fulvestrant in a single injection of about or less than 1.5 ml of formulation.

Yet another object of the invention is the provision of an intramuscular injection dosage form of fulvestrant capable of delivering up to and/or in excess of 500 mg of fulvestrant in a single injection of less than or about 5 ml of formulation.

An even further object of the invention is the provision of an intramuscular injection dosage form of fulvestrant capable of delivering up to and/or in excess of 500 mg of fulvestrant in a single injection of less than or about 2 ml of formulation.

Still further objects of the invention will be appreciated by those of ordinary skill in the art once familiar with the disclosures set forth herein.

BRIEF SUMMARY OF THE INVENTION

In a first embodiment of the invention in which a dosage form suitable for administering currently recommended therapeutic doses of up to 250 mg of fulvestrant as a single injection or in two injections, the forgoing and other objects of the invention can be achieved by a composition comprising (1) fulvestrant in a concentration of at least 40 mg/ml in (2) a solvent or solvent system, wherein said solvent or solvent system is selected from the group consisting of glycofurol, polyethylene glycol, poloxamer, reverse poloxamer, propylene glycol, dihydrolipoic acid and mixtures thereof as well as substantially non-aqueous solutions thereof provided that (a) glycofurol or dihydrolipoic acid be a constituent of the solvent system or (b) if neither glycofurol nor dihydrolipoic acid is a component of the solvent system then the solvent system contain at least polyethylene glycol in combination with at least one of a poloxamer, a reverse poloxamer, or propylene glycol; and (3) optionally containing other compatible excipients with the proviso that the formulations are substantially free of, preferably completely free of, castor oil and castor oil derivatives. These formulations are preferably administered intramuscularly, but can be administered by suitable injection routes that are suitable for the fulvestrant active agent, or via transdermal administration or topical administration.

In a second embodiment of the invention, the foregoing and other objects of the invention can be achieved by substantially higher concentrations of fulvestrant in a solvent or solvent system selected from the same group as set forth above for the first embodiment except that propylene glycol can only be present if at least one of glycofurol or dihydrolipoic acid is present or if the solvent system is polyethylene glycol/propylene glycol in the absence of a substantial amount of poloxamer or reverse poloxamer.

In both of the foregoing embodiments, castor oils and castor oil derivatives such as partially and fully hydrogenated versions of castor oil or polyethoxylated versions of either are substantially absent, if not totally absent, as defined further herein below.

BRIEF DESCRIPTION OF THE SEVERAL VIEWS OF THE DRAWING

Not Applicable

DETAILED DESCRIPTION OF THE INVENTION

The present invention is directed to formulations of fulvestrant that are primarily designed for intramuscular injection, although other injection routes that are compatible with fulvestrant and the excipients are also contemplated as within the invention. In addition, administration by transdermal or topical administration where desired are also within the scope of the invention. The main features of the invention formulation are (1) fulvestrant is contained within the formulation in a concentration of at least 40 mg/ml, preferably in a first embodiment at a concentration of about 45 to about 60 mg/ml, more preferably about 50 mg/ml and in a second embodiment in excess of 50 mg/ml generally up to about 500 mg/ml (although even higher concentrations are achievable), preferably about 75 mg/ml or more, more preferably about 100 mg/ml or more, other preferred amounts including about 150 mg/ml or more, about 200 mg/ml or more, about 250 mg/ml, about 300 mg/ml or more, about 375 mg/ml or more, about 400 mg/ml or more, about 450 mg/ml or more, and about 500 mg/ml or more, although concentrations greater than about 300 mg/ml are generally too viscous for intramuscular injection, such formulations remain suitable for topical and transdermal administration of fulvestrant; (2) the formulation contains a solvent or mixed solvent system selected from the group consisting of (A) (i) glycofurol, (ii) dihydrolipoic acid, and (iii) mixtures thereof; each alone or (B) mixtures of any of the foregoing with one or more materials selected from the group consisting of polyethylene glycol, poloxamer, reverse poloxamer, and propylene glycol, or (C) polyethylene glycol in combination with either a poloxamer, a reverse poloxamer or or propylene glycol, although this section (C) solvent groups containing propylene glycol are only suitable up to concentrations of up to fulvestrant 50 mg/ml; in further optional combination with additional compatible solvents; (3) optionally additional pharmaceutically acceptable and compatible non-solvent excipients; and (4) the formulations are at least substantially free of castor oil and castor oil derivatives or completely free of castor oil and castor oil derivatives.

In other words, the solvent systems require use of one of glycofurol, glycofurol/polyethylene glycol,
glycofurol/propylene glycol,
glycofurol/polyethylene glycol/propylene glycol,
glycofurol/poloxamer,
glycofurol/poloxamer/propylene glycol,
glycofurol/reverse poloxamer,
glycofurol/reverse poloxamer/propylene glycol,
glycofurol/poloxamer/polyethylene glycol,
glycofurol/poloxamer/polyethylene glycol/propylene glycol,
glycofurol/reverse poloxamer/polyethylene glycol,
glycofurol/reverse poloxamer/polyethylene glycol/propylene glycol,
glycofurol/poloxamer/reverse poloxamer,
glycofurol/poloxamer/reverse poloxamer/polyethylene glycol,
glycofurol/poloxamer/reverse poloxamer/propylene glycol,
glycofurol/poloxamer/reverse poloxamer/polyethylene glycol/propylene glycol,
dihydrolipoic acid,
dihydrolipoic acid/polyethylene glycol,
dihydrolipoic acid/propylene glycol,
dihydrolipoic acid/polyethylene glycol/propylene glycol,
dihydrolipoic acid/poloxamer,
dihydrolipoic acid/poloxamer/propylene glycol,
dihydrolipoic acid/reverse poloxamer,
dihydrolipoic acid/reverse poloxamer/propylene glycol,
dihydrolipoic acid/poloxamer/polyethylene glycol,
dihydrolipoic acid/poloxamer/polyethylene glycol/propylene glycol,
dihydrolipoic acid reverse poloxamer/polyethylene glycol,
dihydrolipoic acid/reverse poloxamer/polyethylene glycol/propylene glycol,
dihydrolipoic acid/poloxamer/reverse poloxamer,
dihydrolipoic acid/poloxamer/reverse poloxamer/polyethylene glycol,
dihydrolipoic acid/poloxamer/reverse poloxamer/propylene glycol,
dihydrolipoic acid/poloxamer/reverse poloxamer/polyethylene glycol/propylene glycol,
glycofurol/dihydrolipoic acid,
glycofurol/dihydrolipoic acid/polyethylene glycol,
glycofurol/dihydrolipoic acid/propylene glycol,
glycofurol/dihydrolipoic acid/polyethylene glycol/propylene glycol,
glycofurol/dihydrolipoic acid/poloxamer,
glycofurol/dihydrolipoic acid/poloxamer/propylene glycol,
glycofurol/dihydrolipoic acid/reverse poloxamer,
glycofurol/dihydrolipoic acid/reverse poloxamer/propylene glycol,
glycofurol/dihydrolipoic acid/poloxamer/polyethylene glycol,
glycofurol/dihydrolipoic acid/poloxamer/polyethylene glycol/propylene glycol,
glycofurol/dihydrolipoic acid reverse poloxamer/polyethylene glycol,
glycofurol/dihydrolipoic acid/reverse poloxamer/polyethylene glycol/propylene glycol,
glycofurol/dihydrolipoic acid/poloxamer/reverse poloxamer,
glycofurol/dihydrolipoic acid/poloxamer/reverse poloxamer/polyethylene glycol,
glycofurol/dihydrolipoic acid/poloxamer/reverse poloxamer/propylene glycol,
glycofurol/dihydrolipoic acid/poloxamer/reverse poloxamer/polyethylene glycol/propylene glycol,
polyethylene glycol/propylene glycol,
poloxamer/polyethylene glycol,
reverse poloxamer/polyethylene glycol,
poloxamer/polyethylene glycol/propylene glycol,
reverse poloxamer/polyethylene glycol/propylene glycol,
poloxamer/reverse poloxamer/polyethylene glycol,
poloxamer/reverse poloxamer/polyethylene glycol/propylene glycol,
and substantially non-aqueous solutions thereof and optionally containing other compatible excipients with the proviso that the formulations are substantially free of, preferably completely free of, castor oil and castor oil derivatives. These formulations are preferably administered intramuscularly, but can be administered by other suitable injection routes that are suitable for the fulvestrant active agent, or via transdermal or topical administration.

In a second embodiment of the invention, the foregoing and other objects of the invention can be achieved by substantially higher concentrations of fulvestrant in a solvent or solvent system selected from the foregoing group of solvent systems except that if propylene glycol is used, it is only used when glycofurol or dihydrolipoic acid is also present, preferably for this embodiment, propylene glycol is not used at all. In other words, for this second embodiment in which greater than 50 mg/ml solutions of fulvestrant in the solvent or solvent system are required, the solvent or solvent system is selected from glycofurol,
glycofurol/polyethylene glycol,
glycofurol/propylene glycol,
glycofurol/polyethylene glycol/propylene glycol,
glycofurol/poloxamer,
glycofurol/poloxamer/propylene glycol,
glycofurol/reverse poloxamer,
glycofurol/reverse poloxamer/propylene glycol,
glycofurol/poloxamer/polyethylene glycol,
glycofurol/poloxamer/polyethylene glycol/propylene glycol,
glycofurol reverse poloxamer/polyethylene glycol,
glycofurol/reverse poloxamer/polyethylene glycol/propylene glycol,
glycofurol/poloxamer/reverse poloxamer,
glycofurol/poloxamer/reverse poloxamer/polyethylene glycol,
glycofurol/poloxamer/reverse poloxamer/propylene glycol,
glycofurol/poloxamer/reverse poloxamer/polyethylene glycol/propylene glycol,
dihydrolipoic acid,
dihydrolipoic acid/polyethylene glycol,
dihydrolipoic acid/propylene glycol,
dihydrolipoic acid/polyethylene glycol/propylene glycol,
dihydrolipoic acid/poloxamer,
dihydrolipoic acid/poloxamer/propylene glycol,
dihydrolipoic acid/reverse poloxamer,
dihydrolipoic acid/reverse poloxamer/propylene glycol,
dihydrolipoic acid/poloxamer/polyethylene glycol,
dihydrolipoic acid/poloxamer/polyethylene glycol/propylene glycol,
dihydrolipoic acid reverse poloxamer/polyethylene glycol,
dihydrolipoic acid/reverse poloxamer/polyethylene glycol/propylene glycol,
dihydrolipoic acid/poloxamer/reverse poloxamer,
dihydrolipoic acid/poloxamer/reverse poloxamer/polyethylene glycol, dihydrolipoic acid/poloxamer/reverse poloxamer/propylene glycol,
dihydrolipoic acid/poloxamer/reverse poloxamer/polyethylene glycol/propylene glycol,
glycofurol/dihydrolipoic acid,
glycofurol/dihydrolipoic acid/polyethylene glycol,
glycofurol/dihydrolipoic acid/propylene glycol,
glycofurol/dihydrolipoic acid/polyethylene glycol/propylene glycol,
glycofurol/dihydrolipoic acid/poloxamer,
glycofurol/dihydrolipoic acid/poloxamer/propylene glycol,
glycofurol/dihydrolipoic acid/reverse poloxamer,
glycofurol/dihydrolipoic acid/reverse poloxamer/propylene glycol,
glycofurol/dihydrolipoic acid/poloxamer/polyethylene glycol,
glycofurol/dihydrolipoic acid/poloxamer/polyethylene glycol/propylene glycol,
glycofurol/dihydrolipoic acid reverse poloxamer/polyethylene glycol,
glycofurol/dihydrolipoic acid/reverse poloxamer/polyethylene glycol/propylene glycol,
glycofurol/dihydrolipoic acid/poloxamer/reverse poloxamer,
glycofurol/dihydrolipoic acid/poloxamer/reverse poloxamer/polyethylene glycol,
dihydrolipoic acid/poloxamer/reverse poloxamer/propylene glycol,
glycofurol/dihydrolipoic acid/poloxamer/reverse poloxamer/polyethylene glycol/propylene glycol,
polyethylene glycol/propylene glycol,
poloxamer/polyethylene glycol,
reverse poloxamer/polyethylene glycol,
poloxamer/reverse poloxamer/polyethylene glycol,
and substantially non-aqueous solutions thereof and optionally containing other compatible excipients with the proviso that the formulations are substantially free of, preferably completely free of, castor oil and castor oil derivatives. These formulations are preferably administered intramuscularly, but can be administered by other suitable injection routes that are suitable for the fulvestrant active agent, or via transdermal or topical administration.

For purposes of the present invention, substantially free, when referencing the amount of a component of a formulation means not more than about 5%, preferably not more than about 4.5%, more preferably not more than about 4%, even more preferably not more than about 3%, still more preferably not more than about 2%, yet more preferably not more than about 1%, still more preferably not more than about 0.5%, even still more preferably not more than about 0.1%, still more preferably not more than about 0.01% (100 ppm), most preferably undetectable amounts with the use of standard analytic equipment as of the filing date of the present specification, (i.e., zero), each of the %s being with reference to the complete formulation. In addition, with reference to the absence of castor oil or castor oil derivative associated side effects, the term "substantially free of" means that the present invention has a significantly lesser rate of incidence of that side effect in test populations as compared to formulations having the same percentage of castor oil as present in the FASLODEX marketed product as sold in the US as of the filing date of the present invention and/or (preferably and) an absolute rate of incidence of such side effect of not more than about 10% of the test population, preferably not more than about 5% of the test population, even more preferably not more than about 2% of the test population, still more preferably not more than about 1% of the test population, even more preferably not more than about 0.5% of the test population.

Alternatively, "substantially free" with respect to the avoidance of side effects also means a reduction in or avoidance of such side effect with respect to the degree of such side effect seen in patients given the present invention as compared to that degree seen in patients generally given similar formulations having castor oil or castor oil derivatives in amounts present in the FASLODEX marketed product as sold in the US as of the filing date of the present invention. Thus, both absolute rate of side effect presentation (described in the previous paragraph) and degree of reduction of that side effect independently can be the basis for "substantial free" when speaking of side effect issues, preferably both incidence and degree of side effect reduction meet these limitations simultaneously. In this context (side effect issues), "substantially free" means less than 20% of that seen with the current marked FASLODEX product (independently with respect to rate of side effect presentation and/or side effect level), preferably less than about 10%, more preferably less than about 7.5%, still more preferably less than about 5%, even more preferably less than about 2.5%, still more preferably less than about 1%, most preferably 0% of that seen with the FASLODEX product. Preferably, the products of the present invention meet each of (1) the absolute amount "substantially free" limitation on castor oil and castor oil derivative and (2) at least one of the "substantially free" limitations (a) on side effect per se or (b) rate of side effect in test populations.

For purposes of the present invention, one must find a solvent or solvent system that is (a) capable of solubilizing fulvestrant to the appropriate degree; (b) be a solvent that is administrable via injection, especially intramuscularly, or via the transdermal or topical route; and (c) that is substantially free of or completely free of the side effects typically attributable to castor oil or castor oil derivatives upon injection. The typical side effects of castor oil and its derivatives are (a) skin and other irritation at the administration site; (b) allergic reaction; and (c) gastrointestinal disturbances even though the product is not administered to the GI tract. While any one or more of these can serve as a basis of improvement, the primary (but not exclusive) measure of whether the invention product is "substantially free" of the "castor oil associated side effects" is skin or injection site irritation. Preferably more than one of these side effects, and most preferably all of these side effects have a lesser rate of presentation and lower severity when present than that seen in the currently US marketed FASLODEX product.

In examining the solubility of fulvestrant, the following table shows that there are few solvents that are truly capable of meeting even the at least 40 mg/ml solubility requirement.

| | |
|---|---|
| Tween 80(1%) | Insoluble |
| Lecithin (1%) | Insoluble |
| Lecithin (1%) | Insoluble |
| Lecithin (1%) | Insoluble |
| Tween 20(1%) | Insoluble |
| Sodium Citrate (30 Mmol) | Insoluble |
| Hydroxy Ethyl Starch (10%) | Insoluble |
| N-Methylpyrrolidone | 864 mg/ml |
| Aq. PVP K-30 solution (40 mg in 2 ml distil water) | Insoluble |
| T-butanol | 194 mg/ml |
| 1,4 Dioxan | 833 mg/ml |
| TPGS 1000 | Insoluble |
| Ethyl acetate | 7.8 mg/ml |
| Peanut Oil | Insoluble |
| Fat emulsion | Insoluble |

-continued

| | |
|---|---|
| Poloxamer (Lutrol f-68)(2% sol in water) | Insoluble |
| Lauryl macrogol - 32 glyceride (Gelucire 44/14 ® by Gattefosse) | Insoluble |
| 10% Ethanol | Insoluble |
| 10% Ethanol (in water) + PEG 400 (1:1) | Insoluble |
| 30% Ethanol (in water) | Insoluble |
| 50% Ethanol (in water) | Insoluble |
| 2% Benzyl alcohol in Water | Insoluble |
| 0.9% Benzyl alcohol in Water | Insoluble |
| Propylene Glycol | 4.0 mg/ml |
| PEG-400 | 22.5 mg/ml |
| 10% Ethanol/0.9% Benzyl alcohol in PEG 400 (50 ml solution contains 10% ethanol and 0.9% benzyl alcohol and QS to 50 ml with PEG 400 (V/V)) | 10 mg/ml |
| 10% Ethanol/0.9% Benzylalcohol/30% PEG 400 in Water (50 ml contains 10% ethanol, 0.9% BA, 30% PEG 400 all (v/v) qs with water) | 10 mg/ml |
| 10% Ethanol/0.9% Benzylalcohol/30% PEG 400/20 mg per ml Lecithin, in Water (50 ml contains 10% ethanol, 0.9% BA, 30% PEG 400 all (v/v) + 20 mg/ml Lecithin and qs with water | 5 mg/ml |
| PEG 400 + PG (1:1) | 50 mg/ml |
| Cetyl alcohol | 20 mg/1 g |
| 20 mg/ml of Lutrol in PG | 22.7 mg/ml |
| 0.8 ml of (20 mg/ml of Lutrol in PEG 400) + 0.2 ml of Propylene Glycol | 50 mg/ml |
| 0.7 ml of (20 mg/ml of Lutrol in PEG 400) + 0.3 ml of Propylene Glycol | 50 mg/ml |
| 20 mg/ml of Lutrol in PEG 400 | 66.7 mg/ml |
| Glycofurol | 400 mg/ml |
| Dihydrolipoic acid | >450 mg/ml |
| 20-50 mg/ml Lutrol in dihydrolipoic acid | >350 mg/ml |
| 50% dihydrolipoic acid/50% lipoic acid | >350 mg/ml |

From the above table, it is clear that of the foregoing list, only N-methylpyrrolidone, t-butanol, PEG 400+propylene glycol (1:1), 2% solution of Lutrol (poloxamer) in PEG 400, 2% solution of Lutrol in PEG 400 with propylene glycol, glycofurol, dihydrolipoic acid, and poloxamer/dihydrolipoic acid solubilize fulvestrant sufficiently to be able to have a final concentration of fulvestrant of at least 40 mg/ml based on the complete formulation, and only those solvent systems having glycofurol or dihydrolipoic acid as a component sufficiently solubilize the fulvestrant to be able to achieve the second embodiment of the present invention of substantially higher concentration formulations (greater than 50 mg/ml), although 2% solution of Lutrol (poloxamer) in PEG 400 falls within the lower end of the second embodiment.

Furthermore, the solubility of fulvestrant in 1:1 PEG 400 and propylene glycol is quite surprising as solubility in neat (100%) propylene glycol was only 4 mg/ml, and in neat (100%) PEG-400 was only 22.5 mg/ml, while in 1:1 PEG-400 and propylene glycol system, the solubility is 50 mg/ml. It is equally surprising that solubility in the Lutrol/PEG400/propylene glycol blends was 50 mg/ml as it was insoluble in the neat 2% Lutrol solution, 4 mg/ml in the neat propylene glycol, and 22.5 mg/ml in the neat PEG 400. It is still additionally surprising that fulvestrant was soluble at 66.7 mg/ml in 2% Lutrol in PEG 400 without the propylene glycol.

While N-methylpyrrolidone and 1.4-dioxane (and even t-butanol) are excellent solubilizers for fulvestrant, each of these have their own significant side effects that make them unsuitable for use in injectable formulations. Advantageously, the present invention permits fulvestrant containing formulations containing up to and in excess of 250 mg/ml fulvestrant. Preferably embodiments contain fulvestrant in amounts of about 45 mg/ml, about 50 mg/ml, about 55 mg/ml, about 60 mg/ml, about 65 mg/ml, about 70 mg/ml, about 75 mg/ml, about 80 mg/ml, about 85 mg/ml, about 90 mg/ml, about 95 mg/ml, about 100 mg/ml, about 105 mg/ml, about 110 mg/ml, about 115 mg/ml, about 120 mg/ml, about 125 mg/ml, about 130 mg/ml, about 135 mg/ml, about 140 mg/ml, about 145 mg/ml, about 150 mg/ml, about 155 mg/ml, about 160 mg/ml, about 165 mg/ml, about 170 mg/ml, about 175 mg/ml, about 180 mg/ml, about 185 mg/ml, about 190 mg/ml, about 195 mg/ml, about 200 mg/ml, about 205 mg/ml, about 210 mg/ml, about 215 mg/ml, about 220 mg/ml, about 225 mg/ml, about 230 mg/ml, about 235 mg/ml, about 240 mg/ml, about 245 mg/ml, about 250 mg/ml, about 275 mg/ml, about 300 mg/ml, about 325 mg/ml, about 350 mg/ml, about 375 mg/ml, about 400 mg/ml, about 425 mg/ml, about 450 mg/ml, about 475 mg/ml, or about 500 mg/ml (although concentrations of 400 mg/ml and higher are generally too viscous for intramuscular injection, these are still suitable for topical and transdermal administration), and can contain lesser amounts per ml if desired as well as any amount falling between any of the specifically recited amounts. Fulvestrant dissolved in 100% glycofurol or in mixtures of glycofurol with PEG or mixtures of glycofurol with poloxamer or fulvestrant dissolved in 100% dihydrolipoic acid or mixtures of poloxamer and dihydrolipoic acid, or mixtures having both glycofurol and dihydrolipoic acid are preferred for concentrations in excess of about 95 mg fulvestrant/ml of formulation. The mixtures may be in any proportion, but is preferred where the glycofurol (for glycofurol containing formulations) or dihydrolipoic acid (for formulations containing dihydrolipoic acid as the solvent) makes up at least 20% of the mixture of solvents. Very highly preferred are 1:1 mixtures of glycofurol with either polyethylene glycol or propylene glycol as are mixtures of 20-50 mg of poloxamer/ml of dihydrolipoic acid and 20-50 mg ploxamer per ml of 1:1 mixture of dihydrolipoic acid and lipoic acid. Other preferred solutions, especially when a solubility of about 50 mg/ml or less is necessary include PEG/propylene glycol (1:1), 2% poloxamer in PEG in combination with propylene glycol (with the propylene glycol making up 20-30% of the solvent system), and 2% poloxamer in PEG. When polyethylene glycol (PEG) is used, it is preferably PEG-200-800, more preferably PEG-400. Another preferred solvent system is poloxamer generally about up to 4%, preferably about 1 to about 3%, more preferably about 2% in polyethyleneglycol, preferably in polyethylene glycol 400, glycofurol, or dihydrolipoic acid or mixtures thereof. Preferred poloxamers include, without limitation poloxamer 188 and poloxamer 421 and the commercial material known as LUTROL (which is poloxamer 188, aka Pluronic F-68). Poloxamers are block copolymers having a central block of polypropyleneoxide bounded on each side by a block of polyethylene oxide. Reverse poloxamers are block copolymers having a central block of polyethyleneoxide bounded on each side by polypropyleneoxide. The reverse poloxamers can generally be used in place of poloxamers in the same proportions as set forth for the poloxamers. The reverse poloxamers and the poloxamers differ slightly in their hydrophilic/hydrophobic nature and those of ordinary skill in the art would be able to make appropriate substitutions between poloxamers and reverse poloxamers for use in the instant invention in light of this specification.

Since a major point of the invention is to avoid the irritation at the administration site, and thus hopefully achieve better compliance with the full regimen recommended for the indications being treated, solubility is not the end of the determination of a suitable solvent or solvent system. Irritation studies, as shown in the table below demonstrate the improvement seen with the present invention glycofurol and glycofurol/PEG formulations.

| Test # | Composition | | Irritation rating |
|---|---|---|---|
| 01 | Labrafac | 1.25 ml | Strongly Irritating |
| | PEG 400 | 0.625 ml | |
| | PG | 0.625 ml | |
| 02 | Glycofurol | | No Irritation |
| 03 | Glycofurol | 0.75 ML | No Irritation |
| | PEG 400 | 0.50 ML | |
| 04 | Glycofurol | 0.625 ML | No Irritation |
| | PEG 400 | 0.625 ML | |
| 05 | Glycofurol | 0.625 ML | Slightly Irritating |
| | PG | 0.625 ML | |
| 06 | PG | | Slightly Irritating |
| 07 | Labrafac | | Strongly Irritating |
| 08 | PEG 400 alone | | No Irritation |
| 09 | Marketed product's solvent system (consists of 10% Ethanol, 10% benzyl alcohol, 15% benzyl benzoate and qs to 100% (v/v) with castor oil) | | Slightly Irritating which is higher than the Glycofurol system and much lower than Labrafac system |

The above tests were conducted by injecting 0.1 ml of solvent system in rat tail vein and observing for signs of irritation. Irritability is graded as per the observations of the behavior of the rat and also the site of injection. If the rat is absolutely restless with continuous movement within the cage, the solvent system is considered as strongly irritation which coincides with the inflammation at the site of injection. Slightly irritating is considered to be the case when the rat's behavior is slightly above the normal movement of the rat.

In addition, a rat paw lick test was conducted to further evaluate the irritation issue and the results are shown in the table below. In this method 0.1 ml of the solvent system is injected on the subplanar paw of the rat and the irritation is measured by the number of time that rat licks its paw over 15 minutes. This is quite quantitative and the number licks correlate to the irritation of the system.

| COMPOSITION | | IRRITABILITY |
|---|---|---|
| Labrafac | 1.25 ml | Strongly Irritating. |
| PEG 400 | 0.625 ml | 30 licks in first 15 minutes |
| PG | 0.625 ml | |
| Glycofurol | | No Irritation |
| | | Zero lick in first 15 minutes |
| Glycofurol | 0.75 ml | No Irritation |
| PEG 400 | 0.75 ml | Zero lick in first 15 minutes |
| Marketed product's solvent system | | Slightly irritating. 6 licks in first 15 minutes |
| Normal Saline control | | Zero licks in 15 minutes |

Of the solvent systems tested in the above tables, only glycofurol or glycofurol/PEG showed no irritation in each test, while the solvent system in the currently marketed Faslodex product (containing castor oil) showed irritation in each of the tests.

Another factor of importance in the inventive formulations is their stability over time so that a commercially reasonable product can be manufactured and introduced into the channels of commerce with sufficient dating as to be commercially reasonable. Generally, a stable product is one which when stored under the directed conditions retains at least 80% of label potency, preferably at least about 90% of labeled potency at a designated date, which is generally at least one year, preferably at least about 18 months, more preferably at least about 2 years, and most preferably even longer. Direct data on stability for the particular time and storage conditions as well as accelerated stability studies as are common in the art can be used to determine the particular formulation stability. An alternative demonstration for stability is based on the area % detection of degradants over the particular time period and storage conditions in question (i.e., direct storage or accelerated stability storage conditions to allow for a dating of the respective time period in question, namely at least one year, preferably at least 18 months, more preferably at least 2 years, most preferably longer). Generally a stable product is one which has not more than a total of area % of degradants of 3% and any one degradant area % of not more than 1%, preferably both total degradant and any one degradant limitations are simultaneously met. Preferably both potency and degradant area % limitations are met.

In some embodiments, some oxidative degradation was seen and incorporation of a compatible antioxidant is of additional value. Suitable non-limiting antioxidants include, without limitation, lipoic acid and its structural analogs such as dihydrolipoic acid, methionine and other sulfur-containing amino acids, acetone sodium bisulfate, propyl gallate, BHT, BHA and sodium formaldehyde sulfoxylate. Preferably the antioxidant is lipoic acid or its structural analogs such as dihydrolipoic acid, and preferably the antioxidant is present in an amount ranging up to about 75 mg/ml, more preferably about 25-75 mg/ml, still more preferably about 50 mg/ml. In addition, dihydrolipoic acid can also be used as a solubilizing agent as well as a carrier solvent, which can further aid to prolong the release of drug as well as reducing the injection volume. Because of these additional uses of dihydrolipoic acid, it may further be used beyond these "antioxidant" limitation amounts all the way up to the amounts indicated as suitable earlier for use as a solvent.

The following examples are presented to exemplify, not limit, the scope of the present invention, which is only limited by the claims appended hereto.

General

The storage condition for the current commercial FASLODEX formulation is 2-8° C. which means that the marketed product needs to be stored under refrigerated conditions. In order to understand the degradation nature of fulvestrant, we conducted stability of fulvestrant in strongly acidic, basic and peroxide media at 60° C. In acid, we stored the samples for 7 days, in base for 5 days and in peroxide for 48 hour. The degradation profile is tabulated below:

| DEGRADENT RRT | Area % DEGRADENT In Acid | Area % DEGRADENT In Base | Area % DEGRADENT In Peroxide |
|---|---|---|---|
| 0.49 | 0.86 | — | — |
| 0.52 | 2.31 | — | — |
| 0.95 | 0.35 | — | — |
| 1.07 | 0.52 | 0.54 | 28.3 |
| 1.12 | 0.86 | — | — |
| 1.18 | — | — | 0.39 |
| 1.20 | — | — | 0.43 |

The data suggest that fulvestrant is susceptible to oxidation and showed a better stability in the basic medium compared the acidic environment. In the next set of experiments, we prepared a simulated version of FASLODEX using the same components as set forth in the FASLODEX label and is shown below:

| | |
|---|---|
| Fulvestrant | 50 mg/mL |
| Ethanol (Dehydrated) | 10% w/v |
| Benzyl Alcohol | 10% w/v |

-continued

| | |
|---|---|
| Benzyl Benzoate | 15% w/v |
| Castor Oil | q.s. to volume. |

The required quantity of fulvestrant was weighed and taken in a Volumetric Flask. Ethanol was added to this and sonicated for 5 min giving a clear solution. Benzyl alcohol and benzyl benzoate were added as per formula and mixed thoroughly to obtain a clear solution. Castor Oil was added to make up the volume. The solution was stored at 40° C. for three months. The purpose of the study is to determine the degradation profile of simulated FASLODEX formulation. The degradation product summary is presented in table 2:

TABLE 2

Degradation profile of simulated innovator product stored at 40° C. for 3 months

| RRT | Impurity Area % | Impurity ID |
|---|---|---|
| 1.06 | 0.26 | Unknown |
| 1.08 | 12.9 | Oxidation |
| 1.16 | 0.25 | Unknown |
| 1.18 | 0.09 | Oxidation |
| 1.20 | 0.15 | Oxidation |

As shown in the table above, the formulation showed significant oxidative degradation. Therefore, we tested several innovative formulations that contain various combinations of drug concentration, PEG400, glycofurol, lutrol with and without antioxidizing agents. The data summarized in the following examples.

Example 1

| | |
|---|---|
| Fulvestrant: | 100 mg/ml |

In a solvent system of

| | |
|---|---|
| Labrofac | 50% |
| PG | 25% |
| PEG 400 | 25% |

The above formulation is stored under the conditions set forth in the Table below and the degradation profile is set out in the Table.

| Storage Temp. | Time period | Content | Initial as 100% | RRT | Impurity Area % |
|---|---|---|---|---|---|
| | Initial | 133.0 | 100 | 1.10 | 0.39 |
| | | | | 1.22 | 0.11 |
| 40 | 90 days | 97.0 | 73 | 1.06 | 0.14 |
| | | | | 1.07 | 0.23 |
| | | | | 1.09 | 0.88 |
| | | | | 1.18 | 0.13 |
| | | | | 1.22 | 0.11 |

The formulation showed a better degradation profile compare to the simulated innovator formulation. We observed 13.7% area percent of degradants in the simulated Falsodex compared to 1.5% of the inventive formulation presented in the Example 1. Moreover a single oxidant peak of 12.8 area percent was observed in the simulated Falsodex formulation.

Example 2

The following formulation was prepared and tested for stability over time.

| | | |
|---|---|---|
| Fulvestrant: in Glycofurol | | 25 mg/ml 100% |

| Storage Temp. | Time period | Content | Initial as 100% | RRT | Impurity Area % |
|---|---|---|---|---|---|
| | Initial | 25.5 | 100 | 1.07 | 0.36 |
| | | | | 1.10 | 0.10 |
| 40° C. | 60 days | 24.1 | 95 | 1.07 | 3.94 |
| | | | | 1.17 | 0.27 |
| | | | | 1.19 | 0.10 |
| | 90 days | 22.3 | 87 | 1.06 | 6.14 |
| | | | | 1.15 | 0.35 |
| | | | | 1.17 | 0.09 |
| | | | | 1.19 | 0.21 |
| 25° C. | 3 months | 24.5 | 96 | 1.06 | 1.22 |
| | | | | 1.15 | 0.05 |
| | | | | 1.17 | 0.09 |
| | 6 months | 24.0 | 94 | 0.07 | 0.13 |
| | | | | 1.08 | 2.40 |
| | | | | 1.21 | 0.11 |
| | | | | 1.23 | 0.12 |
| | 12 months | 23.1 | 91 | 1.07 | 6.49 |
| | | | | 1.14 | 0.12 |
| | | | | 1.16 | 0.33 |
| | | | | 1.18 | 0.16 |
| | | | | 1.19 | 0.72 |
| | | | | 1.21 | 0.18 |
| | | | | 1.23 | 0.26 |
| | | | | 1.24 | 0.25 |
| | | | | 1.25 | 0.15 |

Fulvestrant showed much better stability in the glycofurol containing medium compared to the mixed solvent system presented in the Example 1. Once again the predominant degradation path is oxidative degradation. More degradant peaks observed at 12 month storage at 25° C. compared to six months sample and the peak at RRT about 1.07 is the major degradant.

Example 3

In the next set of experiments, we prepared fulvestrant at 150 mg/ml in glycofurol and its stability was evaluated. The purpose of this experiment is to evaluate whether higher concentration of fulvestrant would affect the stability.

| Storage Temp. | Time period | Content | Initial as 100% |
|---|---|---|---|
| | Initial | 157.7 | 100 |
| 40° C. | 30 days | 88.3 | 56 |
| | 60 days | 82.4 | 52 |
| | 90 days | 74.2 | 47 |
| 25° C. | 3 months | 150.4 | 95 |

This formulation showed inferior stability compared to Example 2 under accelerated conditions.

Example 4 & Example 5

Since 150 mg/ml fulvestrant in glycofurol showed poor stability compared to 25 mg/ml under accelerated conditions, we have conducted the stability of fulvestrant at 75 mg/ml and 50 mg/ml in glycofurol. The stability data presented in the tables below:

| 50 MG/ML | | | |
|---|---|---|---|
| Storage Temp. | Time period | Content mg/ml | Initial as 100% |
| | Initial | 47.8 | 100 |
| 40° C. | 30 days | 47.0 | 98 |
| | 60 days | 45.6 | 95 |
| | 90 days | 42.8 | 90 |
| 25° C. | 3 months | 45.6 | 95 |
| | 6 months | 45.4 | 95 |
| | 12 months | 44.5 | 93 |

| 75 MG/ML | | | |
|---|---|---|---|
| Storage Temp. | Time period | Content mg/ml | Initial as 100% |
| | Initial | 77.8 | 100 |
| 40° C. | 30 days | 74.9 | 96 |
| | 60 days | 70.5 | 91 |
| | 90 days | 67.5 | 87 |
| 25° C. | 3 months | 74.9 | 96 |
| | 6 months | 71.2 | 92 |
| | 9 months | 69.0 | 89 |

The 75 mg/ml and 50 mg/ml formulations show better stability than the concentrated 150 mg/ml formulation.

Example 6

We have also studied the stability of fulvestrant at 200 mg/ml in a solvent system that contained 50% glycofurol/50% propylene glycol. The stability data presented in the table below

| Storage Temp. | Time period | Content mg/ml | Initial as 100% |
|---|---|---|---|
| | Initial | 198.0 | 100 |
| 40° C. | 30 days | 197.0 | 100 |
| | 60 days | 195.2 | 99 |
| | 90 days | 191.6 | 97 |
| 25° C. | 3 months | 198.5 | 100 |
| | 6 months | 195.0 | 98.5 |
| | 12 months | 187.0 | 94.4 |

Fulvestrant showed outstanding stability in this system. The accelerated stability data indicate that this formulation is stable for 2 years at room temperature storage. Also, we did not find any significant levels of oxidative degradation this system, suggesting that the combination of propylene glycol and glycofurol surprisingly prevents the oxidative degradation. This is quite unusual as both these solvents are known to promote the oxidation.

Example 7

We have also studied the stability of fulvestrant at 100 mg/ml in a solvent system that contained 50% glycofurol/50% PEG 400. The stability data presented in the table below

| Storage Temp. | Time period | Content mg/ml | Initial as 100% | Area % of oxidative degredant |
|---|---|---|---|---|
| | Initial | 94.5 | 100 | 0 |
| 40° C. | 30 days | 92.8 | 98 | 0.7 |
| | 60 days | 92.8 | 98 | 1.0 |
| | 90 days | 89.7 | 94 | 1.1 |
| 25° C. | 3 months | 95.6 | 101 | 0 |
| | 6 months | 94.4 | 100 | 0.8 |
| | 12 months | 92.3 | 98 | 1.2 |

The stability of fulvestrant in this system is comparable to glycofurol/PG containing system.

Example 8

Since fulvestrant undergoes oxidation, we also have evaluated the effect of an antioxidizing agent on the stability of the formulation of Example 7. 50 mg/ml lipoic acid was also incorporated into the system. The stability data is presented in the table below:

| Storage Temp. | Time period | Content | Initial as 100% | Area % of oxidative degredant |
|---|---|---|---|---|
| | Initial | 100.1 | 100 | 0 |
| 40° C. | 30 days | 97.6 | 98 | 0 |
| | 60 days | 97.5 | 97 | 0 |
| | 90 days | 95.2 | 95 | 0 |
| 25° C. | 90 days | 98 | 98 | 0 |
| | 6 months | 98 | 98 | 0 |
| | 12 months | 97 | 97 | 0 |

We have conducted bioequivalence study comparing this formulation with the innovator product. The composition of the formulation we tested is as follows:

| Ingredients | per 2.5 ml |
|---|---|
| Fluvestrant | 250 |
| PEG-400 | 1.25 ml |
| Glycofurol | 1.25 ml |
| α-lipoic acid | 125 mg |

The test results suggest that our formulation does sustain drug in the circulation for 28 days, like the currently marketed FASLODEX product formulation.

Example 9

A 50 mg/ml fulvestrant formulation using dihydrolipoic acid as a solvent is prepared having the following components and amounts:

| Fulvestrant: | 50 mg |
|---|---|
| Dihydrolipoic acid, quantity sufficient to make→ | 1 ml |

50 mg of fulvestrant weighed into a 1 ml volumetric flask and dissolved by adding 0.5 ml of dihydrolipoic acid. After complete dissolution, the contents of the flask made to the volume by adding dihydrolipoic acid.

Example 10

A 100 mg/ml fulvestrant formulation using dihydrolipoic acid as a solvent is prepared having the following components and amounts:

| | |
|---|---|
| Fulvestrant: | 100 mg |
| Dihydrolipoic acid, quantity sufficient to make→ | 1 ml |

100 mg of fulvestrant is weighed into a 1 ml volumetric flask and dissolved by adding 0.5 ml of dihydrolipoic acid. After complete dissolution, the content of the flask is made to the volume by adding dihydrolipoic acid.

Example 11

A 150 mg/ml fulvestrant formulation using dihydrolipoic acid as a solvent is prepared having the following components and amounts:

| | |
|---|---|
| Fulvestrant: | 150 mg |
| Dihydrolipoic acid, quantity sufficient to make→ | 1 ml |

150 mg of fulvestrant is weighed into a 1 ml volumetric flask and dissolved by adding 0.5 ml of dihydrolipoic acid. After complete dissolution, the content of the flask is made to the volume by adding dihydrolipoic acid.

Example 12

A 250 mg/ml fulvestrant formulation using dihydrolipoic acid as a solvent is prepared having the following components and amounts:

| | |
|---|---|
| Fulvestrant: | 250 mg |
| Dihydrolipoic acid, quantity sufficient to make→ | 1 ml |

250 mg of fulvestrant is weighed into a 1 ml volumetric flask and dissolved by adding 0.5 ml of dihydrolipoic acid and sonicating the contents of flask for 2 minutes. After complete dissolution, the content of the flask is made to the volume by adding dihydrolipoic acid.

Example 13

A 350 mg/ml fulvestrant formulation using dihydrolipoic acid as a solvent is prepared having the following components and amounts:

| | |
|---|---|
| Fulvestrant: | 350 mg |
| Dihydrolipoic acid, quantity sufficient to make→ | 1 ml |

350 mg of fulvestrant is weighed into a 1 ml volumetric flask and dissolved by adding 0.5 ml of dihydrolipoic acid and sonicating the contents of flask for 5 minutes and heating to 60° C. for 10 minutes. After complete dissolution, the content of the flask is made to the volume by adding dihydrolipoic acid.

Example 14

A 500 mg/ml fulvestrant formulation using dihydrolipoic acid as a solvent is prepared having the following components and amounts:

| | |
|---|---|
| Fulvestrant: | 500 mg |
| Dihydrolipoic acid, quantity sufficient to make→ | 1 ml |

500 mg of fulvestrant is weighed into a 1 ml volumetric flask and dissolved by adding 0.5 ml of dihydrolipoic acid and sonicating the contents of flask for 10 minutes and heating to 60° C. for 30 minutes. After complete dissolution, the content of the flask is made to the volume by adding dihydrolipoic acid.

Example 15

A 250 mg/ml fulvestrant formulation using dihydrolipoic acid/poloxamer as a solvent is prepared having the following components and amounts:

| | |
|---|---|
| Fulvestrant | 250 mg |
| Lutrol | 20 mg |
| Dihydrolipoic acid, quantity sufficient to make→ | 1 ml |

20 mg of lutrol is weighed into a 1 ml volumetric flask and dissolved by adding 0.5 ml of dihydrolipoic acid. 250 mg of fulvestrant is added to the flask and the contents of the flask is dissolved by sonicating the flask for 10 minutes and heating to 60° C. for 10 minutes. After complete dissolution, the content of the flask is made to the volume by adding dihydrolipoic acid.

Example 16

A 250 mg/ml fulvestrant formulation using dihydrolipoic acid/poloxamer as a solvent with additional lipoic acid as antioxidant is prepared having the following components and amounts:

| | |
|---|---|
| Fulvrestrant | 250 mg |
| Lutrol | 20 mg |
| Lipoic Acid | 100 mg |
| Dihydrolipoic acid, quantity sufficient to make→ | 1 ml |

20 mg of lutrol and 100 mg of lipoic acid are weighed into a 1 ml volumetric flask and dissolved by adding 0.5 ml of dihydrolipoic acid. 250 mg of fulvestrant is added to the flask and the content of the flask is dissolved by sonicating the flask for 10 minutes and heating to 60° C. for 10 minutes. After complete dissolution, the contents of the flask is made to the volume by adding dihydrolipoic acid.

Example 17

A 250 mg/ml fulvestrant formulation using dihydrolipoic acid/polyethylene glycol as a solvent is prepared having the following components and amounts:

| | |
|---|---|
| Fulvestrant: | 250 mg |
| PEG 400 | 0.5 ml |
| Dihydrolipoic acid, quantity sufficient to make→ | 1 ml |

250 mg of fulvestrant is weighed into a 1 ml volumetric flask and dispersed by adding 0.5 ml of PEG 400. The contents of the flask are dissolved by adding 0.3 ml of dihydrolipoic acid and sonicating the contents of flask for 2 minutes. After complete dissolution, the content of the flask is made to the volume by adding dihydrolipoic acid.

Example 18

A 250 mg/ml fulvestrant formulation using dihydrolipoic acid/poloxamer/polyethylene glycol as a solvent is prepared having the following components and amounts:

| | |
|---|---|
| Fulvestrant: | 250 mg |
| PEG 400 | 0.5 ml |
| Lutrol | 20 mg |
| Dihydrolipoic acid, quantity sufficient to make→ | 1 ml |

250 mg of Fulvestrant and 20 mg of lutrol are weighed into a 1 ml volumetric flask and dispersed by adding 0.5 ml of PEG 400. The contents of the flask are dissolved by adding 0.3 ml of dihydrolipoic acid and sonicating the contents of flask for 2 minutes. After complete dissolution, the content of the flask is made up to volume by adding dihydrolipoic acid.

I claim:

1. A substantially non-aqueous fulvestrant formulation, comprising at least 40 mg/ml fulvestrant dissolved in a substantially non-aqueous solvent system which comprises glycofurol, said formulation being substantially free of castor oil and castor oil derivatives.

2. The fulvestrant formulation of claim 1, that is stable at about 25° C. for a period of at least one year.

3. The fulvestrant formulation of claim 2, that is stable at about 25° C. for a period of at least two years.

4. The fulvestrant formulation of claim 2, wherein stability is measured by decomposition of said fulvestrant and is deemed stable when at least 80% of the label amount remains in said formulation at the end of said period.

5. The formulation of claim 1, wherein said pharmaceutically acceptable vehicle further comprises a solvent selected from the group consisting of polyethylene glycol, propylene glycol, dihydrolipoic acid and mixtures thereof, alone or optionally in combination with up to 4% poloxamer and/or reverse poloxamer, said poloxamer % based on the total of the other solvents present, and optionally at least one antioxidant.

6. The formulation of claim 5, wherein said polyethylene glycol is selected from polyethylene glycol 200 to polyethylene glycol 800.

7. The formulation of claim 5, wherein said polyethylene glycol is polyethylene glycol 400.

8. The formulation of claim 1 wherein said fulvestrant is present in an amount selected from about 45 mg/ml, about 50 mg/ml, about 55 mg/ml, about 60 mg/ml, about 65 mg/ml, about 70 mg/ml, about 75 mg/ml, about 80 mg/ml, about 85 mg/ml, about 90 mg/ml, about 95 mg/ml, about 100 mg/ml, about 105 mg/ml, about 110 mg/ml, about 115 mg/ml, about 120 mg/ml, about 125 mg/ml, about 130 mg/ml, about 135 mg/ml, about 140 mg/ml, about 145 mg/ml, about 150 mg/ml, about 155 mg/ml, about 160 mg/ml, about 165 mg/ml, about 170 mg/ml, about 175 mg/ml, about 180 mg/ml, about 185 mg/ml, about 190 mg/ml, about 195 mg/ml, about 200 mg/ml, about 205 mg/ml, about 210 mg/ml, about 215 mg/ml, about 220 mg/ml, about 225 mg/ml, about 230 mg/ml, about 235 mg/ml, about 240 mg/ml, about 245 mg/ml, about 250 mg/ml, about 275 mg/ml, about 300 mg/ml, about 325 mg/ml, about 350 mg/ml, about 375 mg/ml, about 400 mg/ml, about 425 mg/ml, about 450 mg/ml, about 475 mg/ml, and about 500 mg/ml.

9. The formulation of claim 5, further comprising at least one antioxidant.

10. The formulation of claim 9, wherein said antioxidant is selected from the group consisting of lipoic acid, dihydrolipoic acid, methionine and other sulfa-containing amino acids, acetone sodium bisulfate, propyl gallate, BHT, BHA and sodium formaldehyde sulfoxylate.

11. The formulation of claim 10, wherein said antioxidant is lipoic acid and is present in an amount of about 25-75 mg/ml.

12. The formulation of claim 11, wherein said antioxidant is lipoic acid and is present in an amount of about 50 mg/ml.

13. A method of improving patient compliance with an intramuscular fulvestrant dosage regimen comprising administering a formulation of claim 1 to a patient in need thereof.

14. A solvent blend for fulvestrant having the ability to dissolve fulvestrant in excess of 40 mg/ml, comprising:
(A) glycofurol alone or in conjunction with one or more members selected from the group consisting of polyethylene glycols, poloxamers, reverse poloxamers, propylene glycol, dihydrolipoic acid, and mixtures thereof;
(B) dihydrolipoic acid alone or in conjunction with one or more members selected from the group consisting of polyethylene glycols, poloxamers, reverse poloxamers, and mixtures thereof;
(C) polyethylene glycol in combination with at least one of a polxamer, a reverse poloxamer, or propylene glycol; and
(D) optionally a compatible co-solvent compatible with fulvestrant;
said solvent blend being substantially free of water, and substantially free of castor oil and castor oil derivatives.

15. A method of administering fulvestrant in a single intramuscular injection in a dose from in excess of 250 mg comprising preparing a formulation of claim 1 having a concentration of fulvestrant in excess of 50 mg/ml and administering the same by intramuscular injection to a patient in need thereof.

16. The method of claim 15, wherein said dose in excess of 250 mg is selected from about 275 mg, about 300 mg, about 325 mg, about 350 mg, about 375 mg, about 400 mg, about 425 mg, about 450 mg, about 500 mg, about 550 mg, about 600 mg, about 650 mg, about 700 mg, about 750 mg, about 800 mg, about 850 mg, about 900 mg, about 950 mg, and about 1000 mg, and said dose is contained in said formulation in a volume of less than about 5 ml.

17. The formulation of claim 1, wherein the glycofurol makes up at least 20% of the solvent system.

18. The formulation of claim 1, wherein the amount of castor oil and castor oil derivatives is not more than 0.1%.

19. The formulation of claim 18, wherein the amount of castor oil and castor oil derivatives is not more than 0.01%.

20. A substantially non-aqueous fulvestrant formulation, comprising at least 40 mg/ml of fulvestrant dissolved in a substantially non-aqueous solvent system which comprises at least 20% glycofurol, said formulation having not more than 0.1% castor oil and castor oil derivatives.

21. The formulation of claim 1, wherein the formulation further comprises benzyl benzoate.

22. The solvent blend of claim 14, wherein the solvent blend further comprises benzyl benzoate.

* * * * *